United States Patent [19]
Zacher, Jr.

[11] 4,093,863
[45] June 6, 1978

[54] TOMOGRAPHIC APPARATUS
[75] Inventor: Albert R. Zacher, Jr., University City, Mo.
[73] Assignee: Artronix, Inc., St. Louis, Mo.
[21] Appl. No.: 773,833
[22] Filed: Mar. 3, 1977
[51] Int. Cl.² .................................... G03B 41/16
[52] U.S. Cl. ............................ 250/445 T; 250/490
[58] Field of Search .............. 250/445 T, 439 R, 444, 250/445 R, 446, 447, 448, 449, 490, 523, 358 R, 358 P, 359, 360

[56] References Cited
U.S. PATENT DOCUMENTS
3,999,073  12/1976  Hounsfield ................. 250/445 T

*Primary Examiner*—Craig E. Church
*Attorney, Agent, or Firm*—Rogers, Eilers & Howell

[57] ABSTRACT

A source of X-rays is mounted so it can move in a predetermined path relative to an object, a detector is mounted so it can move in a second path relative to that object, the predetermined path has a fixed center, and the predetermined path is so interrelated with the second path that a predetermined point on the source and a predetermined point on the detector define a succession of translated parallel lines, which pass through the object, as the source and the detector move, respectively, through the predetermined and second paths.

24 Claims, 21 Drawing Figures

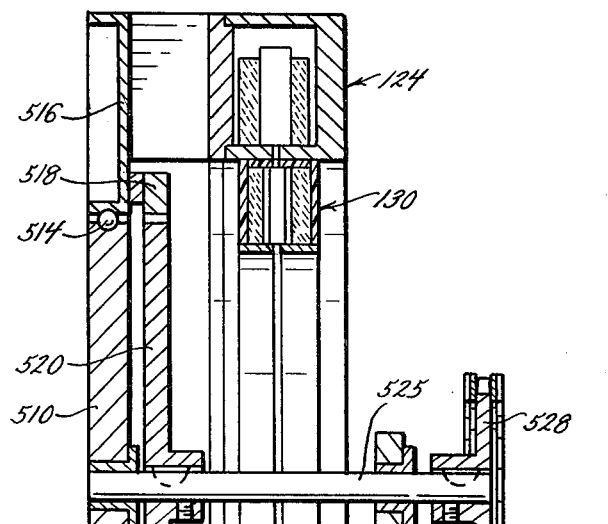
FIG. 21.
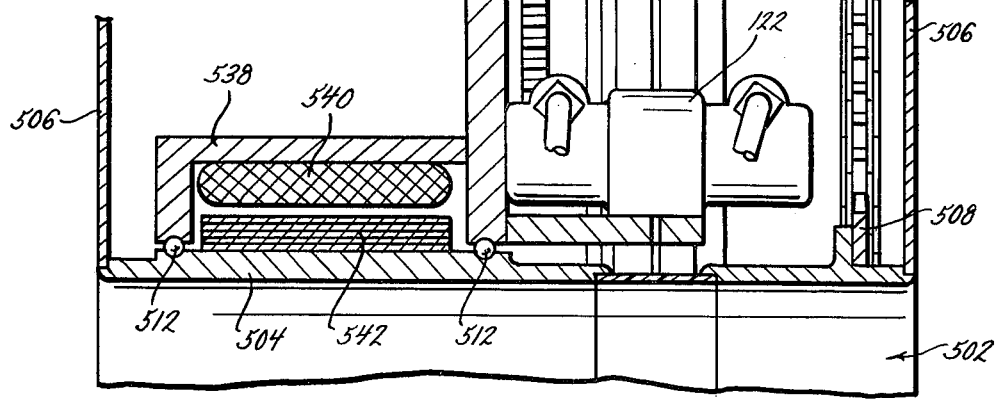
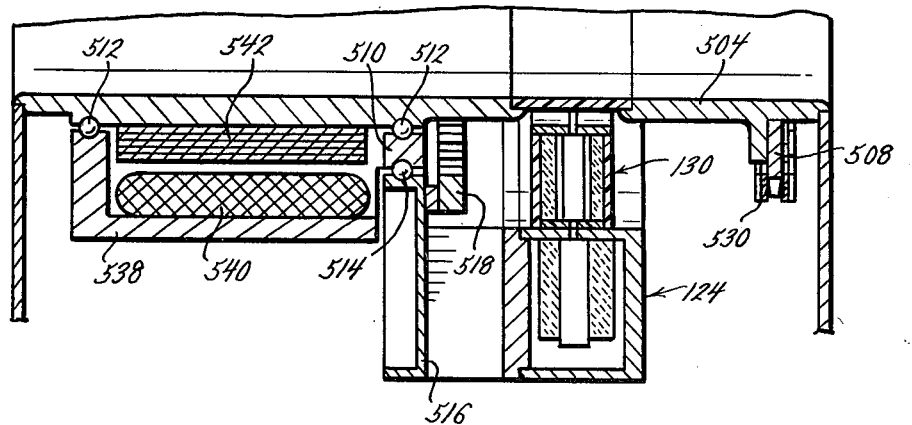

TOMOGRAPHIC APPARATUS

BACKGROUND AND SUMMARY OF THE INVENTION

In a tomograph of the type used in reconstructive tomography, a beam of radiation passes through an object; and a detector receives that beam. Relative movement is provided between the beam of radiation and the object to provide a proper tomographic examination of that object.

Zacher application Ser. No. 636,104 for X-Ray Detector which was filed on Nov. 28, 1975, the disclosure of which is incorporated by reference herein, shows and describes an X-ray tomograph wherein an X-ray source is mounted on a rotatable support at one side of an object-receiving area and wherein a detector is mounted on that rotatable support at the opposite side of that object-receiving area. Rotation of that rotatable support relative to that object-receiving area enables pulsed X-ray beams from that X-ray source to be rotated relative to an object within the object-receiving area while those X-ray beams are passing through that object. That rotatable support is continuously rotatable in one direction; and the object can be repositioned axially at the end of each complete rotation of that rotatable support. As a result, an examination sequence of several rotations of that rotatable support can be conducted on a continuous basis. The X-ray tomograph of the Zacher application is valuable and useful. However, rotating reconstructive tomographs of the type having the relationship between the detector and the radiation source fixed have inherent artifact problems. See G. N. Hounsfield, "Picture Quality of Computed Tomography," *American Journal of Roentgenology*, Vol. 129, pp 3-9 (1976).

The present invention improves the X-ray tomograph of the said Zacher application by mounting the X-ray tube so it can move in a predetermined path relative to the object-receiving space by giving the predetermined path of the X-ray tube a center, by mounting the detector so it can move in a second path relative to that object-receiving space, bygiving the detector a center which moves in the path of the X-ray tube, and by interrelating the movement of that X-ray tube and of that detector so the source of the X-ray beam and a point on that detector define a succession of translated, parallel lines, which pass through the object-receiving space, as that X-ray tube and that detector move, respectively, through the predetermined and second paths. Such construction eliminates artifacts of the type disclosed by Hounsfield and greatly reduces problems caused by inconsistent detector calibration.

Other and further objects and advantages of the present invention should become apparent from an examination of the drawing and accompanying description.

In the drawing and accompanying description, preferred embodiments of the present invention are shown and described but it is to be understood that the drawing and accompanying description are for the purpose of illustration only and do not limit the invention and that the invention will be defined by the appended claims.

DESCRIPTION OF THE DRAWING

In the drawing,

FIG. 6 is a sectional view, on a large scale, through part of the X-ray tomograph of FIG. 1, and it is taken along the plane indicated by the line 6—6 of FIG. 2;

FIG. 21 is a partial cross-section on a large scale of an alternative embodiment similar to that shown in FIG. 15, but using an annular motor as an alternative drive means.

Figure 1:
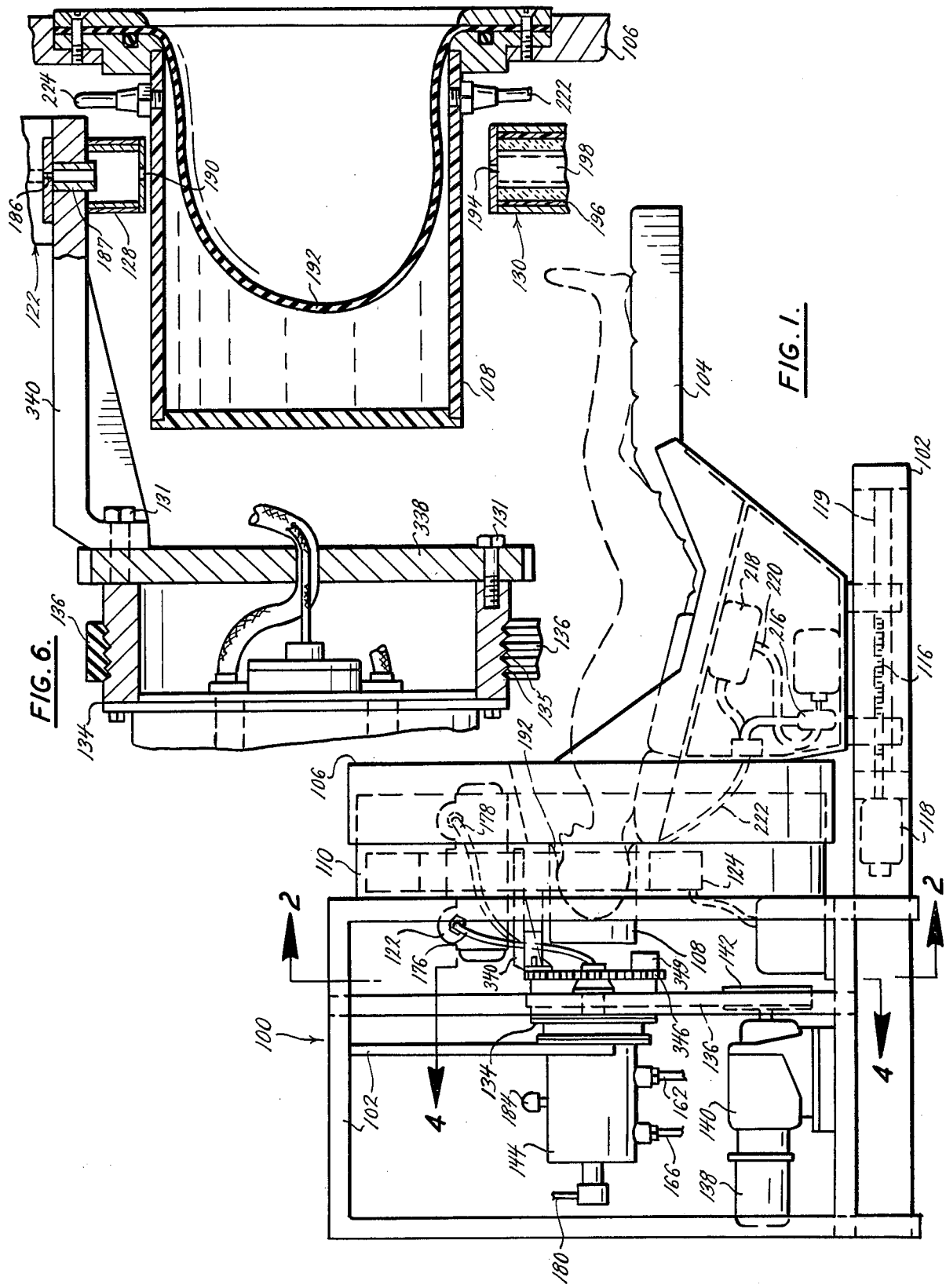
FIG. 1 is a side elevational view of one preferred embodiment of X-ray tomograph which is made in accordance with the principles and teachings of the present invention.

DESCRIPTION OF PREFERRED EMBODIMENTS:

Referring particularly to FIGS. 1-13, the numeral 100 generally denotes an axial X-ray tomograph which is made in accordance with the principles and teachings of the present invention. That X-ray tomograph has a frame 102; and a movable couch 104 is supported by that frame. That couch is connected with a shield 106 and with a head tank 108, and that head tank receives objects to be X-rayed. A shield 110 is mounted on the frame 102. A lead screw 116 in the frame 102 is used to drive the couch 104; and that lead screw is driven in opposite directions by a servo motor 118 to reciprocate that couch relative to sliding supports 119. The movable couch 104, the shield 106, the head tank 108, the shield 110, the lead screw 116, the servo motor 118, and the sliding supports 119 can, and preferably will, be identical to, and will perform in the same manner as, the similarly-numbered components of the Zacher application.

The numeral 134 denotes a drive boss which is rotatably mounted on the frame 102. That drive boss differs from the identically-numbered drive boss in the said application, but it will preferably be rotatably mounted on that frame in the manner disclosed in said application.

The numberal 136 denotes a wide, plural V-belt which engages contiguous V-shaped grooves 135 in the exterior of the drive boss 134. That belt, and hence that drive boss, is driven by a motor 138, a transmission 140, and a sheave 142. The numeral 144 denotes a power housing which is held stationary by the frame 102. The numeral 184 denotes a sight glass for that power housing. The belt 136, the motor 138, the transmission 140, and sheave 142, the power housing 144, and the sight glass 184 can, and preferably will, be identical to, and will perform in the same manner as, the similarly-numbered components of the said Zacher application.

The numerals 162, 176 and 178 denote electric cables; and the numerals 166 and 180 denote electrical conductors. The numeral 192 denotes a rubber cap which is disposed within the head tank 108. The numeral 216 denotes a water pump, the numeral 218 denotes a water reservoir, the numeral 220 denotes tubing, and the numerals 222 and 224 denote tubes. Those electric cables, those electrical conductors, that rubber cap, that water pump, that water reservoir, that tubing, and those tubes can, and preferably will, be identical to and will perform in the same manner as, the similarly-numbered components of the Zacher application.

Figure 3:
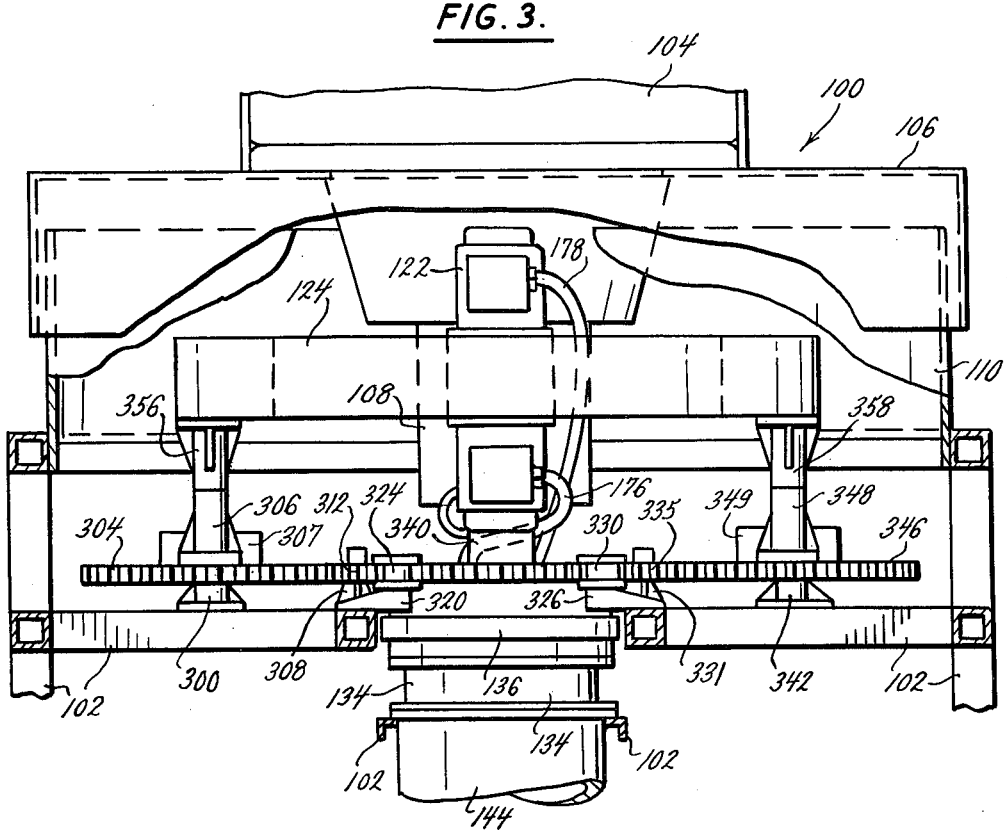
FIG. 3 is a sectional view, on a still larger scale, through the X-ray tomograph of FIG. 1, and it is taken along the plane indicated by the line 3—3 of FIG. 2.
Figure 4:
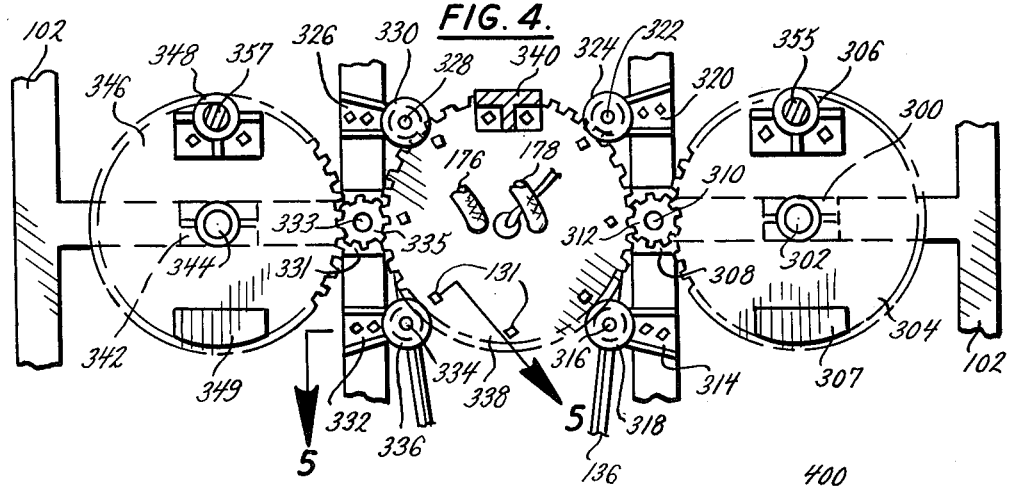
FIG. 4 is a sectional view, on a scale intermediate those of FIGS. 1 and 2, through part of the X-ray tomograph of FIG. 1, and it is taken along the plane indicated by the line 4—4 in FIG. 1.
Figure 5:
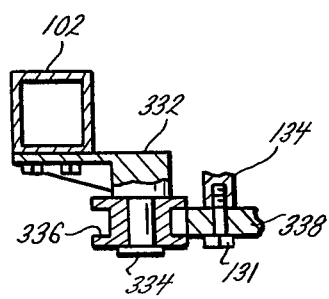
FIG. 5 is a sectional view, on a much larger scale, through part of the X-ray tomograph of FIG. 1, and it is taken along the broken plane indicated by the broken line 5—5 in FIG. 4.

The numeral 300 in FIGS. 3 and 4 denotes a pivot block which is supported by the frame 102; and the numeral 304 denotes a gear that is rotatably supported on a pivot 302 which is held by that pivot block. That gear has an eccentrically-mounted pivot socket 306 and a counterweight 307, all as shown by FIGS. 3 and 4. The numeral 308 denotes a pivot block which is supported by the frame 102; and the numeral 312 denotes a small gear that is rotatably mounted on a pivot 310 which is held by that pivot block. The teeth on the gears 304 and 312 mesh. The numeral 314 denotes a pivot block which is secured to the frame 102 below the level of the pivot block 308, as indicated by FIG. 4; and the former pivot block supports a pivot 316. A gear 318 with annular flanges thereon is rotatably mounted on that pivot. The numeral 320 denotes a pivot block which is secured to the frame 102 above the level of the pivot block 308; and the former pivot block supports a pivot 322. A gear 324 with annular flanges thereon is rotatably mounted on that pivot. The numeral 326 denotes a pivot block which is supported by the frame 102 to the left of, and at the same level as, the pivot block 320 in FIG. 4. A pivot 328 which is held by the former pivot block rotatably supports a gear 330 with annular flanges thereon. The numeral 332 denotes a pivot block which is supported by the frame 102 below the level of the pivot block 326; and the former pivot block is spaced to the left of, and at the same level as, the pivot block 314 in FIG. 4. A pivot 334 which is held by the former pivot block rotatably supports a gear 336 with annular flanges thereon, as shown particularly by FIG. 5. The numeral 331 denotes a pivot block which is supported by the frame 102 to the right of, and at the same level as, the pivot block 308 in FIG. 3. A pivot 333 which is held by the former pivot block rotatably supports a small gear 335.

The numeral 338 denotes a large gear which has the teeth thereof meshing with the teeth of all of the gears 318, 324, 330 and 336; and that gear is supported by the teeth of those gears. Moreover, the annular flanges on the gears 318, 324, 330 and 336 hold the gear 338 against axial movement. As a result, the gear 338 is held for rotation about a virtual center and is held against axial movement. The teeth on the gear 338 also mesh with the teeth on the gear 312. The numeral 340 denotes a bracket which is bolted to, and which rotates with, the gear 338; and that bracket is shown partially in section and partially in side elevation in FIG. 6. A rectangular slot window 186 is mounted on that bracket and a primary shield 187 is mounted within an opening in that bracket, all as shown by FIG. 6. A slit collimator 128 is mounted on the bracket 340 adjacent that primary shield; and the outlet slit 190 of that slit collimator is in register with the rectangular slot window 186. That rectangular slot window, that primary shield, and that slit collimator can, and preferably will, be substantially identical to, and will perform in the same manner as, the similarly-numbered rectangular slot window, primary shield and slit collimator in the said Zacher application.

The numeral 342 denotes a pivot block which is secured to the frame 102 at the same level as the pivot blocks 300, 308 and 331. A pivot 344 which is held by the former pivot block rotatably supports a gear 346 that has the teeth thereof meshed with the teeth of the gear 335. The former gear has an eccentrically-mounted pivot socket 348 and a counterweight 349 thereon, all as shown by FIGS. 3 and 4.

The numeral 122 denotes an X-ray tube that is mounted on the bracket 340 which is bolted to the large gear 388. That bracket will hold that X-ray tube in register with the head tank 108 as the gear 338 rotates that bracket relative to that head tank. The X-ray tube 122 can, and preferably will, be identical to, and will perform in the same manner as, the similarly-numbered X-ray tube in the said Zacher application.

Figure 7:
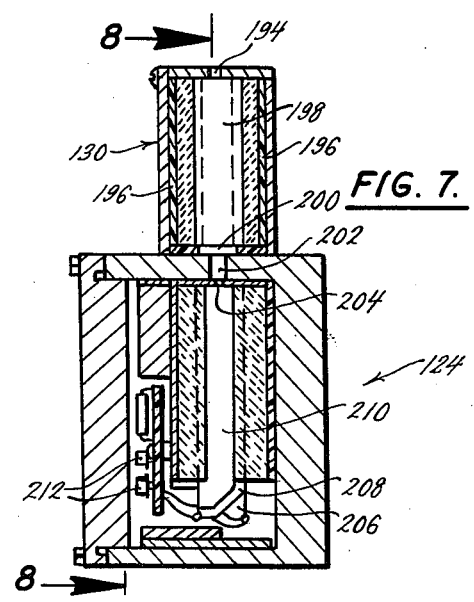
FIG. 7 is a vertical sectional view, on the scale of FIG. 2, through part of the detector of the X-ray tomograph of FIG. 1.

The numeral 124 denotes an X-ray detector which is annular in form, as indicated particularly by FIGS. 2 and 9–13. That detector has a circumferentially-extending inlet slot 202 therein, and also has a circumferentially-extending window 204 which is in register with, but which is narrower than, the slot 202. Radially-oriented metal plates 206 and 208 are mounted within the detector 124; and those plates are alternated. The plates 208 are reference plates which are maintained at ground potential; and the plates 206 are maintained at a potential of negative three kilovolts relative to ground potential. Thin non-metallic plates 210 are secured to the opposite faces of the plates 208; and the exposed surfaces of those non-metallic plates are coated with a metal such as vaporized aluminum. One of those non-metallic plates is shown in FIG. 7; but those non-metallic plates are too thin to be shown in FIG. 8. The metal on the exposed surfaces of the non-metallic plates 210 will constitute ion sensors. The numeral 212 denotes sequentially-firing electronic switches which are parts of an integrated amplifier circuit, not shown. The inlet slot 202, the window 204, the plates 206, 208 and 210, and the sequentially-firing electronic switches 212 can, and preferably will be, substantially identical to, and will perform in the same manner as, the similarly-numbered components of the detector in the said Zacher application.

Figure 2:
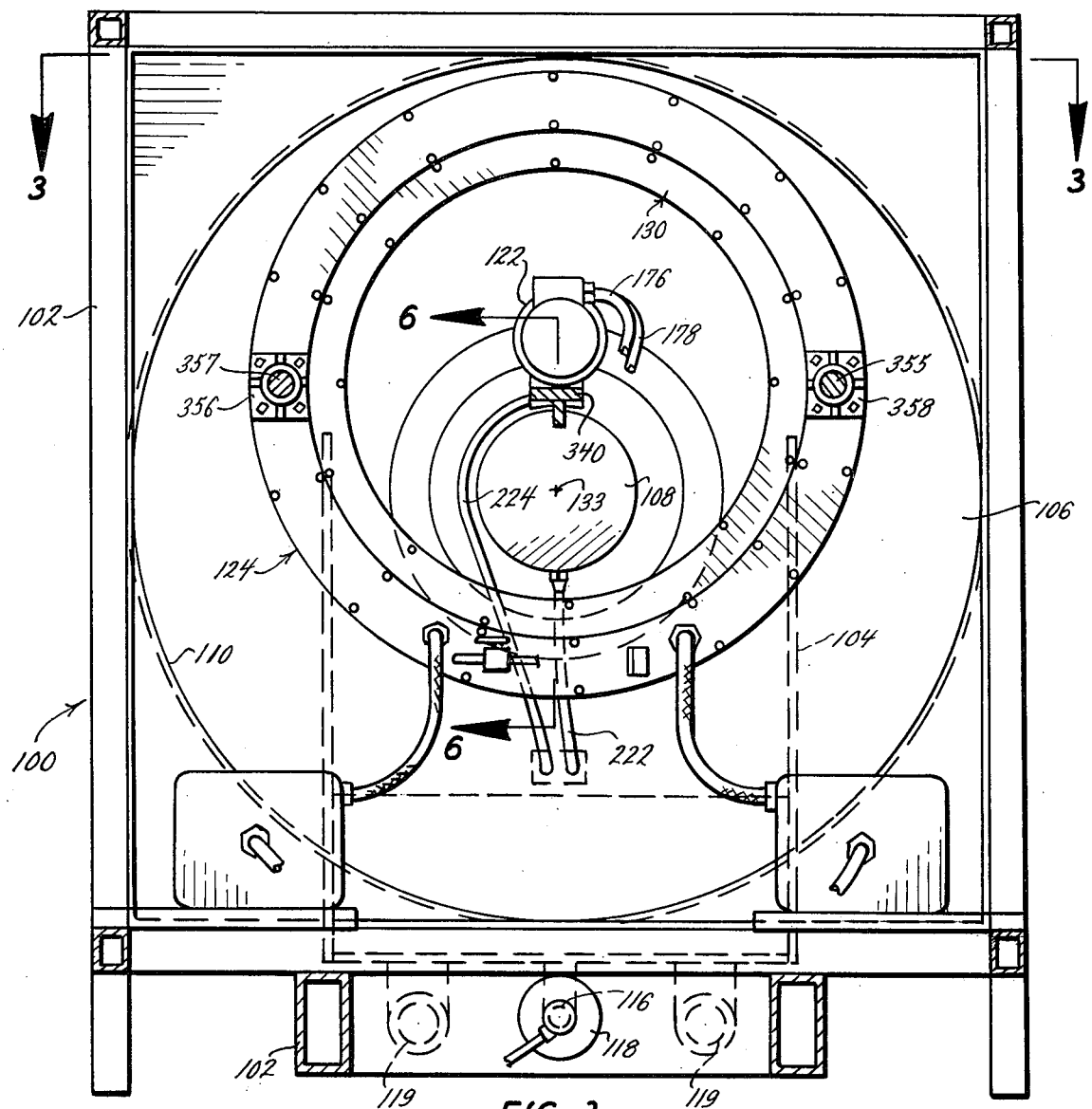
FIG. 2 is a sectional view, on a larger scale, though the X-ray tomograph of FIG. 1, and it is taken along the plane indicated by the line 2—2 of FIG. 1.
Figure 8:
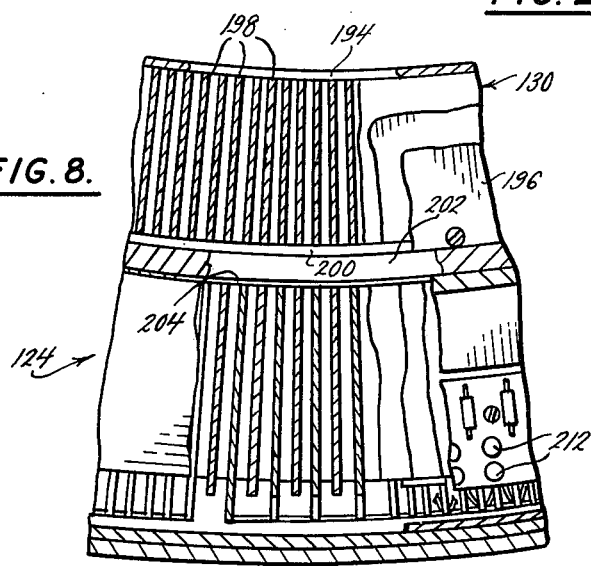
FIG. 8 is a sectional view, on the scale of FIG. 2, through part of the detector shown in FIG. 7, and it is taken along the broken plane indicated by the broken line 8—8 in FIG. 7.

The detector 124 is not secured to, and does not rotate, with the bracket 340 or the gear 338 which support and rotate the X-ray tube 122. Instead, the detector 124 has pivot sockets 356 and 358 secured thereto, as indicated by FIGS. 2 and 3; and pivots 357 and 355, respectively, which are held by those pivot sockets extend into the eccentrically-mounted pivot sockets 306 and 348 on the gears 304 and 346, respectively. As a result, the detector 124 is supported by the gears 304 and 346; and it will move through a path which is defined by the paths of the eccentrically-mounted pivot sockets 306 and 348. This means that the X-ray tube 122 will move, about the head tank 108, in a circular path which has a fixed center; whereas the detector 124 will move about the head tank. Hence, that X-ray tube will move in a predetermined arcuate path about the head tank while that detector moves in a second path about that head tank.

The numeral 130 denotes a scatter collimator which is annular in configuration, and which is mounted on and supported by the detector 124. As shown particularly by FIGS. 2, 7 and 8, that scatter collimator is disposed inwardly of, but in abutting relation with, the detector 124. That scatter collimator has a circumferentially-extending inlet slit 194 and a circumferentially-extending outlet slit 200. Further, that collimator has a lead lining 196. Scatter collimator plates 198 are disposed within the scatter collimator 130; and those scatter collimator plates are aligned with the plates 206 and 208 in the detector 124. Further, the scatter collimator plates 198 and the plates 206 and 208 in detector 124 are all disposed radially of the geometric center of the annular detector 124. The circumferentially-extending inlet slit 194, the circumferentially-extending outlet slit 200, the lead lining 196, and the scatter collimator plates 198 can, and preferably will, be substantially identical to, and will perform the same functions as, the similarly-numbered components of the scatter collimator of the said Zacher application.

As indicated particularly by FIG. 6, the large gear 338 is secured to the drive boss 134 by machine screws 131, and hence will rotate with that drive boss. If desired, that drive boss and the mounting therefor could be made sturdy enough to constitute the sole support for the gear 338; and, in such event, the pivot brackets 314, 320, 326 and 332, the pivots 316, 322, 328 and 332, and the gears 318, 324, 330 and 336 could be eliminated. The gear 338 will respond to rotation of drive boss 134 to rotate both of the gears 312 and 335; and the gear 312 will rotate the gear 304 while the gear 355 will rotate the gear 346. The gear 338 also will rotate the gears 318, 324, 330 and 336; but those gears do not transmit motion and, instead, merely serve as rotatable supports which fix the radial and axial positions of the gear 338. The gears 312 and 355 act as idler gears, so that all of the gears 304, 338 and 346 rotate in the same direction and at the same angular rate.

To use the tomographic apparatus of FIGS. 1–13, the motor for pump 216 will be energized to cause that pump to transfer water from the head tank 108 into the water reservoir 218. The resulting expansion of the rubber cap 192 will facilitate the insertion of a patient's head within that cap, and hence within the head tank 108. That patient will lie on his or her back on the couch 104 and will move his or her head into position within the rubber cap 192. Thereafter, the motor for pump 216 will be energized to cause that pump to transfer water back into the head tank 108 to press the rubber cap 192 closely around the patient's head to immobilize it.

The motor 138 then will be energized, and power will be applied to the X-ray tube 122. The X-rays from the source within that X-ray tube will pass through the rectangular slot window 186, through the primary shield 187, and through the slit collimator 128 to become a fan-shaped planar beam that has an angular extent of about 90°. In all positions of the X-ray tube 122, that fanshaped planar beam will pass though the head tank 108 and the patient's head, and then will pass through the scatter collimator 130 to enter the detector 124. The energization of motor 138 will cause that motor to act through the transmission 140, the sheave 142, the belt 136, and the drive boss 134 to rotate the gear 338. The bracket 340 will respond to each revolution of the gear 338 to force the X-ray tube 122 to rotate successively from the position of FIG. 9 through the positions of FIG. 10, FIG. 11, FIG. 12, FIG. 13, and then back to the position of FIG. 9, — a nominal zero position. Each of the gears 304 and 346 will respond to each revolution of gear 338 to make one complete revolution; and, as the former gears rotate, they will cause the pivots 357 and 355 to follow arcuate paths around axes which are spaced from, but which are parallel to, the axis of rotation 133 of the X-ray tube 122. Those pivots will move through those arcuate paths at the same angular rate at which the X-ray tube 122 moves about its axis of rotation. The pivots 355 and 357 support detector 124; and hence they will cause it to move successively from the position of FIG. 9 through the positions of FIG. 10, FIG. 11, FIG. 12, FIG. 13, and then back to the position of FIG. 9. This means that both the X-ray tube 122 and the detector 124 move relative to the head tank 108.

The X-ray tube 122 moves through a circular path which is concentric with the axis 133 of the drive boss 134; and hence that X-ray tube moves through an arcuate path which has a fixed center. The pivots 355 and 357 move eccentrically of the axis 133, which serves as the fixed center for the path followed by the X-ray tube 122; and hence they force the detector 124 to move through an arcuate path. As shown particularly by FIGS. 9 and 10, the X-ray tube 122 rotates concentrically in the clockwise directon about the axis 133 of the drive boss 134, as it moves from the position of FIG. 9 to the position of FIG. 10. whereas the detector 124 moves downwardly and to the right as it moves from the position of FIG. 9 to the position of FIG. 10. That detector 124 will continue to move downwardly and to the right from the 45° position of FIG. 10 to the 90° position of FIG. 11; and the X-ray tube 122 will rotate concentrically in the clockwise direction about axis 133 from that 45° position to that 90° position. The detector 124 will move downwardly and to the left from the 90° position of FIG. 11 to the 150° position of FIG. 12; and the X-ray tube 122 will rotate concentrically in the clockwise direction about axis 133 from that 90° position to that 150° position. The detector 124 will continue to move downwardly and to the left until it reaches a position which is 180° from the position of FIG. 9; and thereafter, until it reaches the 270° position of FIG. 13, it will move upwardly and to the left. The X-ray tube 122 will, of course continue to rotate concentrically in the clockwise direction between the positions of FIGS. 12 and 13. In moving from the position of FIG. 13 back to the position of FIG. 9, the detector 124 will move upwardly and to the right; and the X-ray tube 122 will continue to rotate concentrically in the clockwise direction.

It is important to note that the source within the X-ray tube 122 moves in the same direction and at the same rate and through the same distance as each and every point on the inner surface of detector 124 during the rotation of the drive boss 134. Consequently, the distances, between that source and all of those points which at any instant are receiving the X-ray beam, remain essentially constant despite that rotation. Also, importantly, a line between that source and a point 139 on the inner surface of detector 124 will translate parallel to itself during the movement of X-ray tube 122 and of detector 124 from a position which is displaced forty-five degrees to the right of the position of FIG. 9 to and through the position of FIG. 9 to the position of FIG. 10. As a result, the portion of the X-ray beam, which is coincident with that line, will translate parallel to itself during that 90° of movement. The line between the source in X-ray tube 122 and the point 139 will be disposed to the right of the patient's head when the detector 124 is displaced 45° to the right of the position of FIG. 9, and that line will be disposed to the left of that patient's head when the detector is in the position of FIG. 10. This means that during the 90° of rotation when a portion of the X-ray beam is coincident with that line, that portion of that X-ray beam will always be parallel to the plates 206 and 208 in detector 124 which define the space into which that portion passes; and, it also means that the said portion of the beam will be translated parallel to itself during that rotation. A corresponding parallelism of beam portion and plates 206 and 208, and a corresponding parallel translation of beam portion will be provided at each and every other point on the inner surface of detector 124. All of this means that the tomographic apparatus provided by the present invention provides parallel translation of the X-ray beam, and all of the advantages consequent thereupon, and yet relies upon rotating components, and all of the advantages consequent thereupon.

A consequence of the relationship between the paths of the detector 124 and the X-ray source 122 is that the center of the detector 124 moves in a fixed path in relation to the path of the X-ray source 122. In the structure shown the two paths are coincident.

The diametral line 137, which passes through the axis 133 of drive boss 134 and through the source of X-ray tube 122, moves circumferentially of the detector 124 as that drive boss rotates that X-ray tube. That diametral line will, at all times, be at the center of the 90° fan-shaped planar X-ray beam from the X-ray tube 122; and hence that fan-shaped planar X-ray beam will move circumferentially of the detector 124. However, because the pviots 355 and 357 move in the same direction, move through the same angular extent, and move through the same distance as the X-ray tube 122, the portions of the fan-shaped planar X-ray beam which are received by each point on the inner surface of detector 124 will translate parallel to themselves throughout the time those portions are passing through a patient's head.

The X-rays which enter the detector 124 interact with xenon or some other suitable ionizable gas between the plates 206 and 208. The resulting charged ions are detected on the plates 210 of the detector 204 and are suitably sensed by a digital computer. The function and operation of the X-ray tube 122 and of the detector 124 will be comparable to those of the similarly-numbered X-ray tube and detector of the said Zacher application. However, because the portions of the X-ray beam provided by the present invention translate parallel to themselves as they pass through the patient's head, whereas the corresponding portions of the X-ray beam provided by the said Zacher application move circumferentially as they pass through the patient's head, the tomographic apparatus provided by the present invention is less sensitive to errors in detector calibration. Further, the effect on the image resulting from detector "afterglow" or "lag" is minimized in the tomographic apparatus of the present invention. The sequencing of plural adjacent scans will proceed as described in the Zacher application.

In the detector and apparatus described in the Zacher application, redundancy in sampling is eliminated by sampling asymmetrically about a line projected from the X-ray source and passing through the center of rotation. In the present device redundancy is eliminated either by sampling, i.e., reading, each detector at positions which are asymmetrical to a line through the center of rotation and parallel to the rays sampled by that detector, or by using an odd number of detectors in the array. The detector plates in the array are aimed at the center of the detector ring, which is also the source of the X-ray beam.

Figure 14:
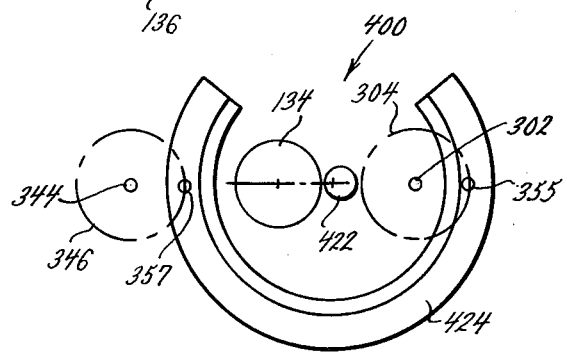
FIG. 14 is a diagrammatic view of a second preferred embodiment of X-ray tomograph which is made in accordance with the principles and teachings of the present invention.
Figure 10:
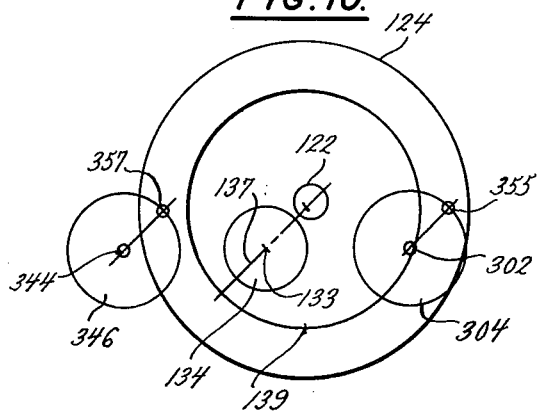
FIGS. 10-13 are smaller-scale kinematic views of the X-ray tomograph of FIG. 1.
Figure 11:
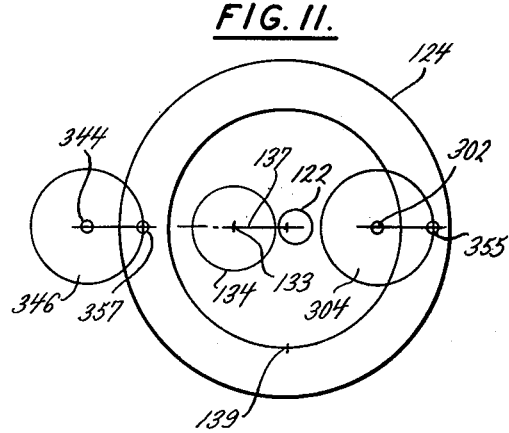
Figure 12:
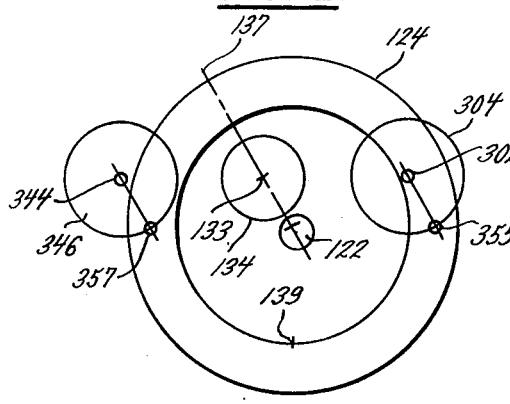
Figure 13:
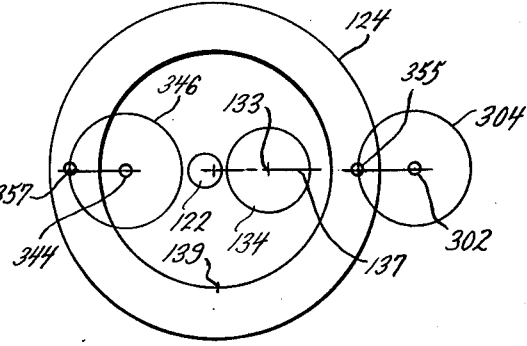
Figure 9:
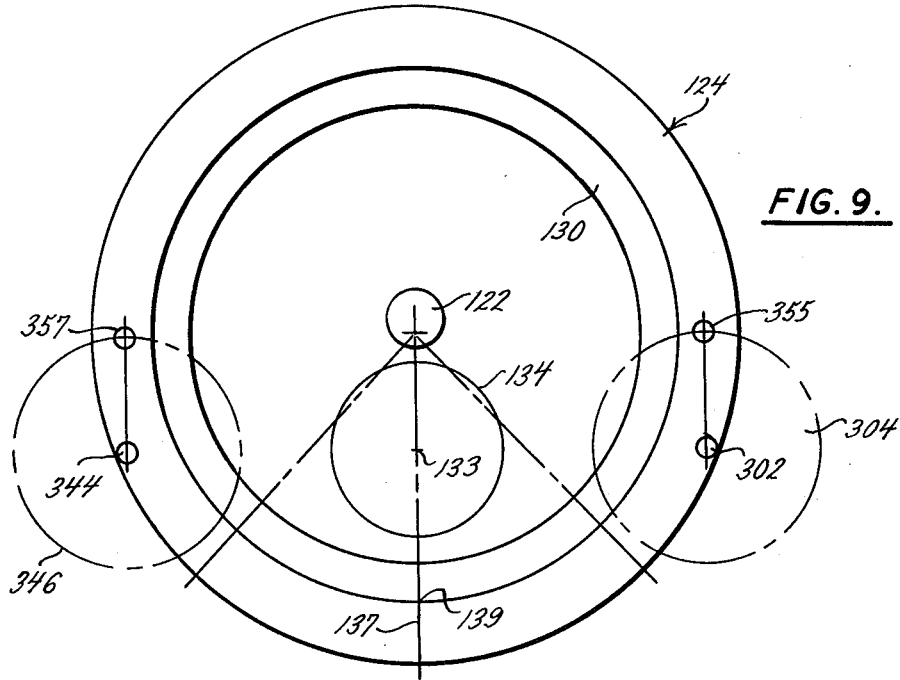
FIG. 9 is a kinematic view of the X-ray tomograph of FIG. 1.

Referring particularly to FIG. 14, the numeral 400 denotes a tomographic apparatus which is generally similar to that of FIGS. 1–13 but which has a detector 424 that has an angular extent of less than 360°. In fact, that detector has an angular extent of slightly less than 270°. The X-ray tube 422 for that tomographic apparatus moves through an arc which has an angular extent slightly greater than 180° but considerably less than 360°. That X-ray tube is supported by a drive boss 134; and the detector 424 is supported by gears 304 and 346 and pivots 355 and 357 — in the same manner in which the X-ray tube and detector of FIGS. 1–13 are supported.

The X-ray tube 422 will provide a fan-shaped planar beam of about 90° angular extent; and that X-ray tube will be moved through an arc of slightly greater than 180°. As a result, all portions of a patient's head can be X-rayed by the tomographic apparatus of FIG. 14. However, that tomographic apparatus provides a sampling which is not as uniform as is the sampling which is provided by the tomographic apparatus of FIGS. 1–13. Furthermore, the tomographic apparatus of FIG. 14 provides no overlap in angular sampling, and the radiation dose is not as uniformly distributed over the section being scanned. However, the tomographic apparatus of FIG. 14 requires less space than does the tomographic apparatus of FIGS. 1–13.

The counterweights 307 and 349 which are shown in FIGS. 3 and 4 are intended to balance and compensate for the weight of the detector 124. Similar counterweights, not shown, for the gears 304 and 345 in FIG. 14 are intended to balance and compensate for the weight of the detector 424. As a result, both of the preferred embodiments of tomograph provided by the present invention will be statically balanced and may be dynamically balanced, if desired.

Figure 15:
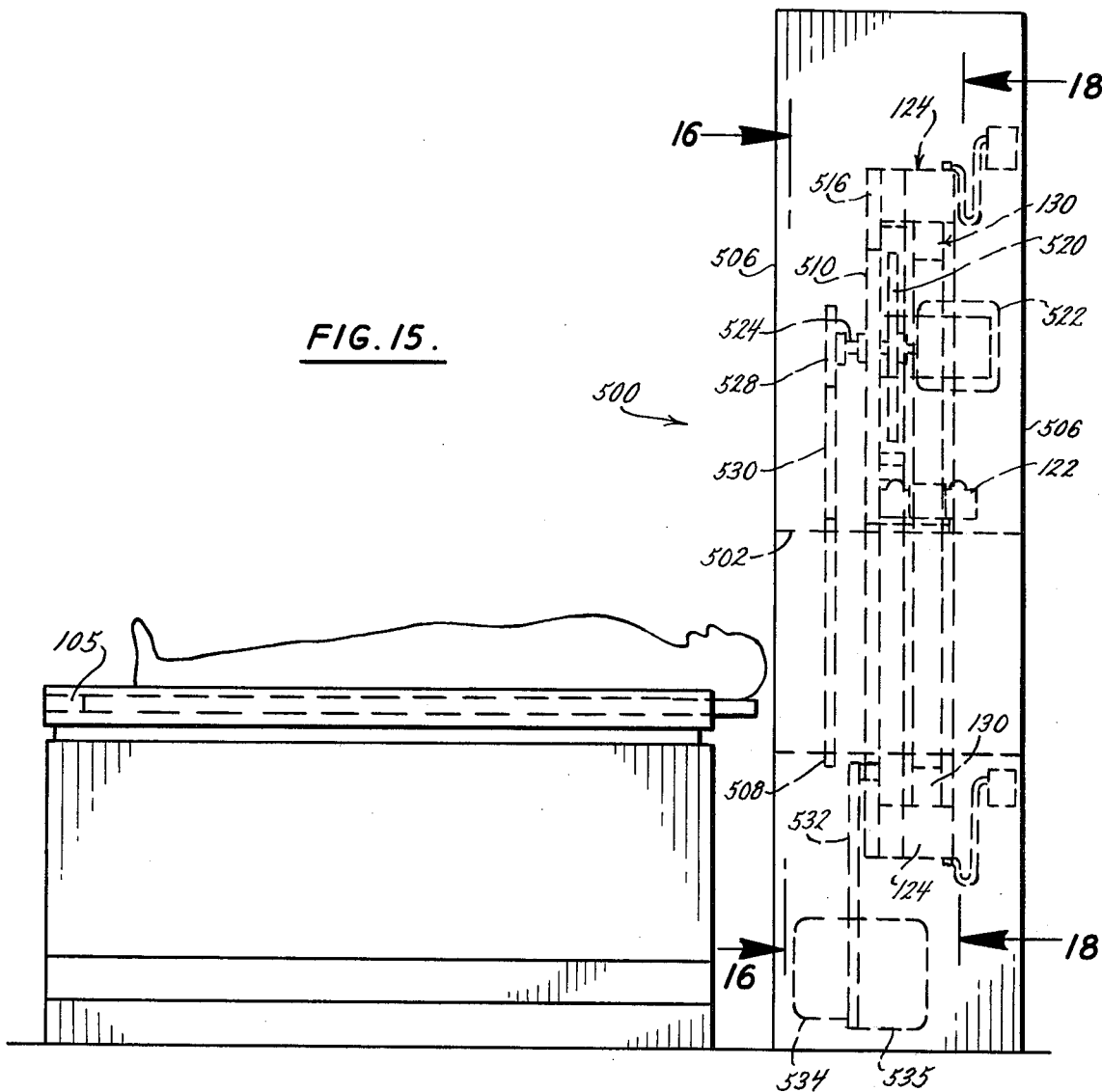
FIG. 15 is a side elevational view of one preferred embodiment of an X-ray tomograph similar to FIG. 1, but in a whole body tomograph form.
Figure 18:
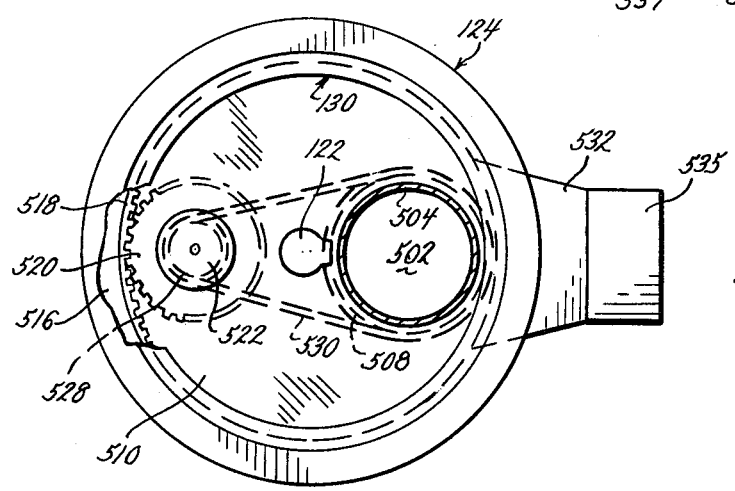
FIG. 18 is a sectional view taken along the plane of line 18—18 in FIG. 15.

FIGS. 15 through 21 show alternative embodiments of the device in which the invention is incorporated in a full body reconstructive tomograph. The operation of the X-ray source, detector, collimator, reconstructive geometry and support equipment is as previously described for the devices of FIGS. 1 through 13. Where possible, the corresponding elements have been marked with the same reference numbers in FIGS. 1-21, for clarity. As shown in FIG. 15, the object to be examined is positioned on a couch 105, which in the case of a full body tomograph, is normally flat. The couch may be driven reciprocally by means, not shown, such as that described for couch 104 of the head scanner 100, or by hydraulic or other means.

The full body tomograph 500 has a correspondingly larger central opening 502, through which the object passes during examination. In the embodiment shown in FIGS. 15 through 18, the motion of the X-ray source 122 and collimator 130 and detector 124, previously described, is achieved by the drive means described herein as follows. Opening 502 through the tomograph is formed by annular tube 504 which is received within mounting plates 506. The annular tube 504 is provided with a surrounding ring gear 508, shown in FIG. 16. Tube 504 is fixed within the tomograph 500 and X-ray source support plate 510, shown in FIG. 17, rotates about tube 504 on bearings 512. The detector 124 and collimator 130 move about the X-ray source support plate 510 on bearings 514, also shown in FIG. 17. Bearings 514 are between X-ray source support plate 510 and the detector and collimator support 516.

Detector and collimator support plate 516 is provided with a ring gear 518 at its inner periphery. Ring gear 518 meshes with and is driven by gear 520, shown in FIG. 17. In the embodiment shown in FIGS. 15 through 18, gear 520 is rotated by motor 522. Shaft 524 of motor 522 also passes through a journal 526 in plate 510 and gear 528 is attached thereto, as shown, and driven thereby. Gear 528 is connected to ring gear 508 by drive chain 530, as shown.

The motion of the X-ray source 122 and detector 124 relative to each other and the examined object in tube 504 is as previously described. When the motor 522 is energized, gears 520 and 528 rotate. Since the tube 504 is held fixed, this rotation drives plate 510 and X-ray source 122 mounted thereon in a circular path that has the center of tube 504 as its center. As support plate 510 rotates, the center of the collimator 130 and detector 124 is caused to rotate by gear 520 in a circular path which has the center of tube 504 as its center. The center of the detector 124 and collimator 130 is, in this embodiment, the point source of the X-rays emanating from X-ray tube 122.

Figure 16:
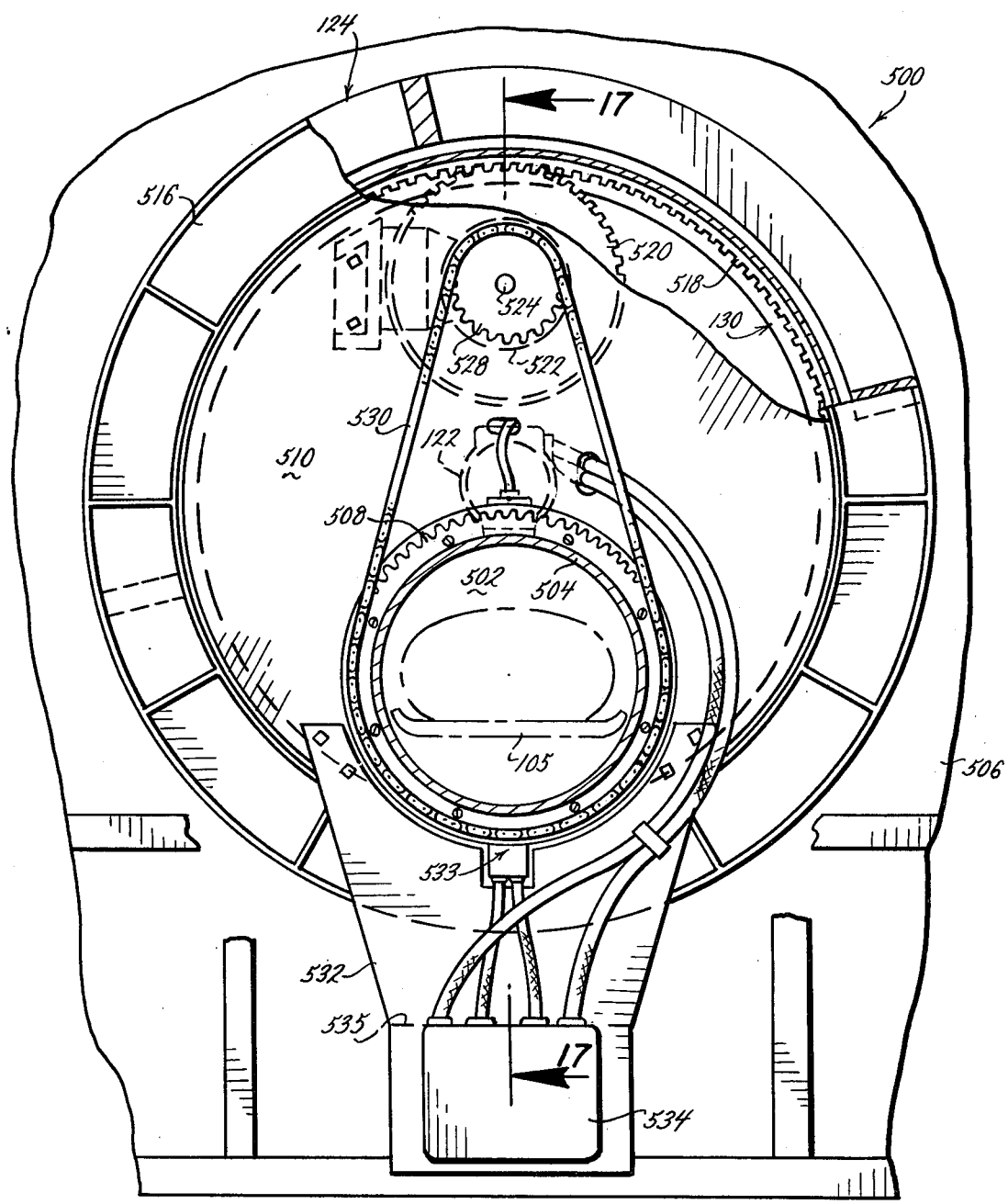
FIG. 16 is a sectional view taken along the plane of the line 16—16 in FIG. 15.
Figure 17:
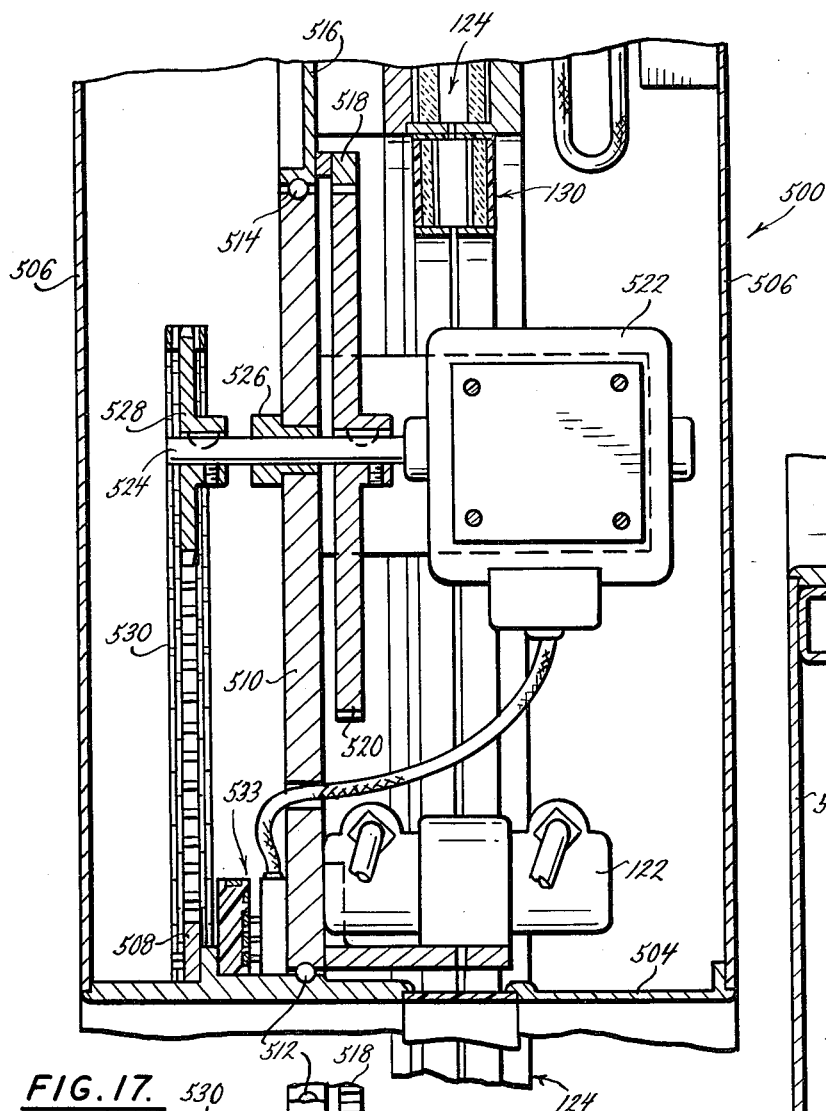
FIG. 17 is a sectional view on a larger scale through the tomograph of FIG. 15 and taken along the plane of the line 17—17 in FIG. 16.

A balance projection 532, shown in FIG. 16, is mounted on plate 510. Projection 532 carries X-ray transformer 534 and other equipment, as desired. This location allows the structure to be balanced. Additional weighting material 535 may be added for complete balance. Power to this equipment can be made by suitable slip ring connections 533.

It should be pointed out that this structure operates in this fashion when the following gear ratios are provided. That is, the ratio of gear 528 to ring gear 508 must equal the ratio of gear 520 to ring gear 518.

Figure 20:
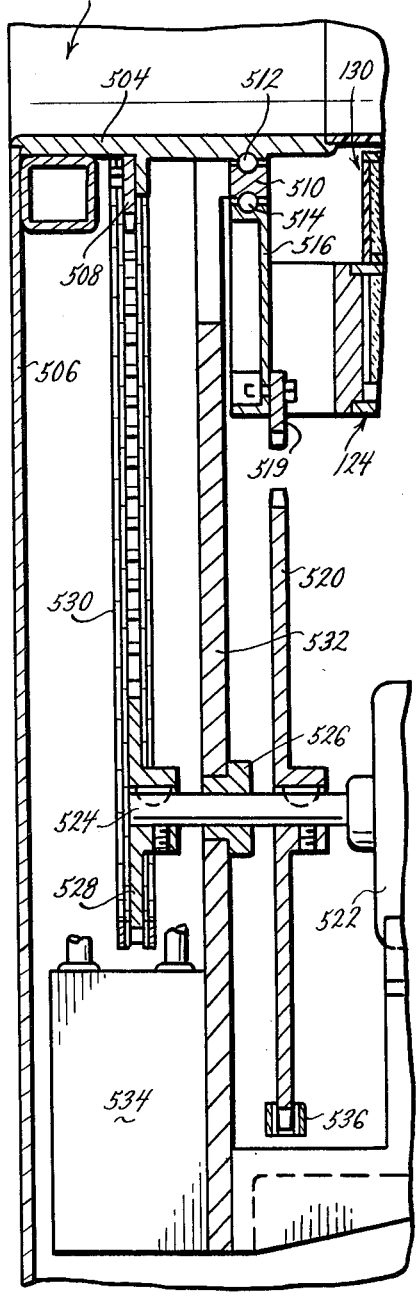
FIG. 20 is a cross-sectional view on a larger scale taken along the plane of lines 20—20 in FIG. 19.
Figure 19:
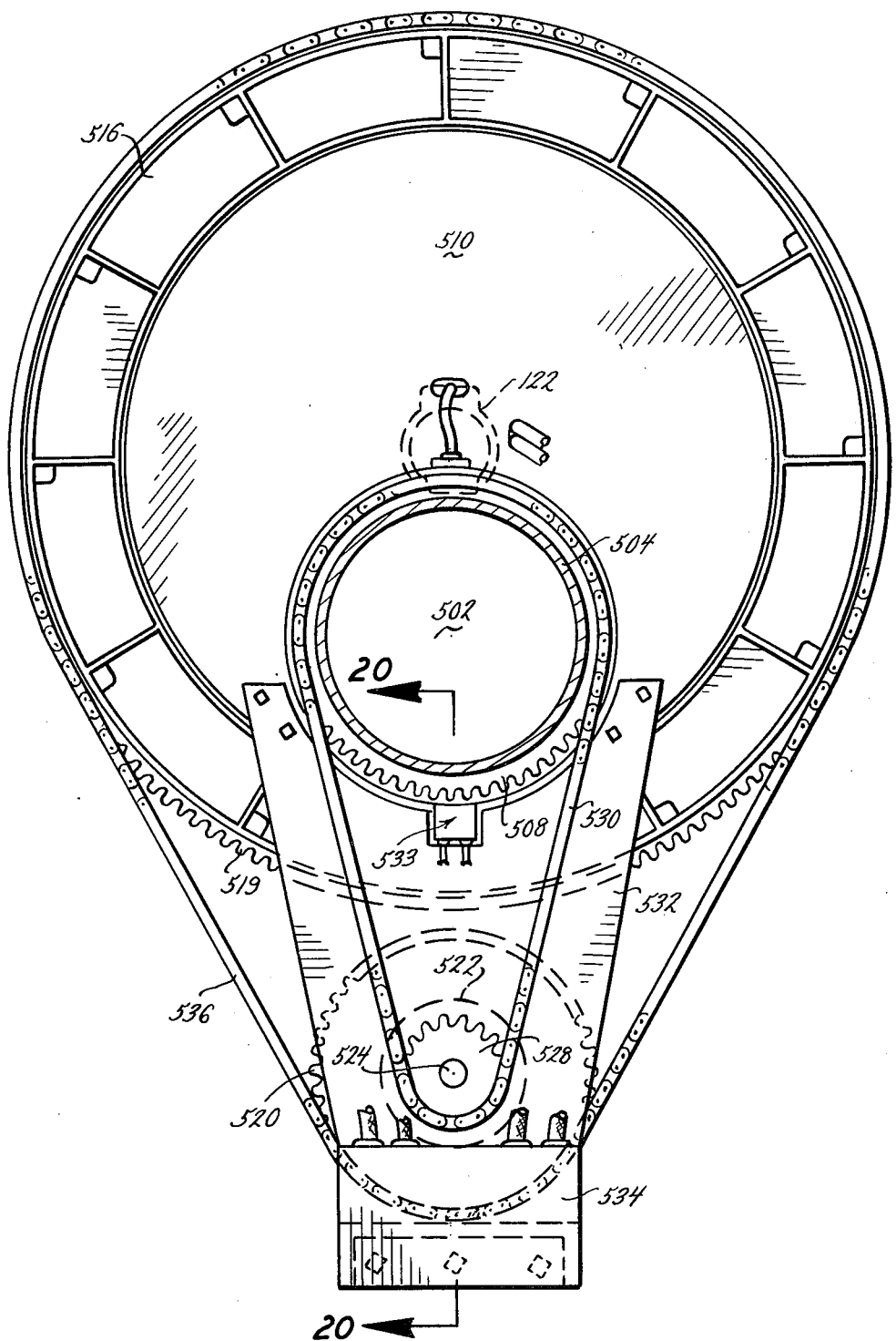
FIG. 19 is a view similar to FIG. 16 of an alternative drive means.

The alternative structure shown in FIGS. 19 and 20 is similar to that shown in FIGS. 15-18, except motor 522 is mounted on balance projection 532. Motor 522 drives both gears 520 and 528. Tube 504 is provided with ring gear 508 and the detector-collimator ring support 516 has an annular ring gear 519 at its outer periphery. In the embodiment shown in FIGS. 19 and 20, gear 528 is connected to ring gear 508 by chain 530. Gear 520 is connected to ring gear 519 by drive chain 526. Transformer 534 may be mounted on extension 532, if desired, to give additional balance. Operation of the device is as described previously for the embodiments shown in FIGS. 1-13 and 15-18. Motor 522 rotates gears 520 and 528. Since tube 504 is fixed, plate 510 and X-ray source 122 mounted thereon rotate about the center of tube 504 and the center of detector 124 and collimator 130, which is at the source point of radiation in X-ray tube 122, and rotate about the center of tube 504. Note that in this embodiment the ratio of gear 520 to ring gear 519 equals the ratio of gear 528 to ring gear 508.

A third embodiment, shown in FIG. 21, is driven by an annular electric motor 538, in which the rotor 540 is fixed to mounting plate 510 and the stator 542 is fixed to annular tube 504. Tube 504 has ring gear 508 which is attached as shown in FIG. 21. Shaft 525 is journaled in plate 510, as shown, and supports gears 528 and 520. The detector and collimator support plate 516 bears ring gear 518 on its inner periphery which meshes with gear 520, as shown. Gear 508 is connected to gear 528 by drive chain 530. In this arrangement it should be noted that the ratio of gear 528 to gear 508 is the same as the ratio of gear 520 to gear 518. Motor 538 rotates plate 510 about the center of tube 504 and also rotates the center of the detector 124 and collimator 130, which is at the source point of radiation of X-ray tube 122, about the center of tube 504 in the manner previously described.

Whereas the drawing and accompanying description have shown and described preferred embodiments of the present invention, it should be apparent to those skilled in the art that various changes may be made in the form of the invention without affecting the scope thereof.

What is claimed is:

1. Apparatus for examining an object by radiation which comprises a support for said object, a source of radiation, a mounting for said source, a detector, a mounting for said detector, said mounting for said source permitting said source to move relative to said object in a predetermined path, said mounting for said detector permitting said detector to move relative to said object in a second path, at least one of said paths being arcuate in at least part thereof, and means to interrelate said predetermined path with said second path so a predetermined point on said source and a predetermined point on said detector define a succession of translated parallel lines, as said source and said detector move, respectively, throughout said predetermined path and said second path.

2. Apparatus as claimed in claim 1 wherein the other of said paths also is, at least in part, arcuate.

3. Apparatus as claimed in claim 1 wherein said one path is circular.

4. Apparatus as claimed in claim 1 wherein said one path is generally concentric to the center of the object.

5. Apparatus as claimed in claim 1 wherein said second path is an orbital path.

6. Apparatus as claimed in claim 1 wherein said detector is arcuate and defines a space in which said source is disposed.

7. Apparatus as claimed in claim 1 wherein said one path is circular, wherein the other of said paths also is, at least in part, arcuate, and wherein said other path is an orbital path having the source of radiation as a center.

8. Apparatus as claimed in claim 1 wherein said source emits penetrating rays, and wherein said detector receives rays which pass from said source to and through said object.

9. Apparatus as claimed in claim 1 wherein eccentrically-mounted pivots support and guide the movement of said detector in said second path.

10. Apparatus as claimed in claim 1 wherein eccentrically-mounted pivots support and guide the movement of said detector in said second path, wherein a rotatable member supports said source, and wherein the moment arm of said source is equal to the moment arm of each of the eccentrically-mounted pivots.

11. Apparatus for examining an object which comprises a support for said object, a source, a mounting for said source, a detector which has a plurality of sensors, a mounting for said detector, said mounting for said source permitting said source to move relative to said object in a predetermined path, said mounting for said detector permitting said detector to move relative to said object in a second path, at least one of said paths being arcuate in at least part thereof, and means to interrelate said predetermined path with said second path so said source is always, throughout the examining of said object, spaced a predetermined distance from at least one of said sensors, said detector being arcuate and defining a space in which said source is enclosed.

12. Apparatus as claimed in claim 11 wherein the other of said paths also is, at least in part, arcuate.

13. Apparatus as claimed in claim 11 wherein said one path is circular.

14. Apparatus as claimed in claim 11 wherein said one path is generally concentric with said object.

15. Apparatus as claimed in claim 11 wherein said one path may be translated axially along the object.

16. Apparatus as claimed in claim 11 wherein said one path is circular, wherein the other of said paths also is, at least in part, arcuate, and wherein the paths may be translated axially along the object.

17. Apparatus as claimed in claim 11 wherein eccentrically-mounted pivots support and guide the movement of said detector in said second path.

18. Apparatus as claimed in claim 11 wherein eccentrically-mounted pivots support and guide the movement of said detector in said second path, wherein a rotatable member supports said source, and wherein the moment arm of said source is equal to the moment arm of each of said eccentrically-mounted pivots.

19. Apparatus as claimed in claim 11 wherein means interrelates said predetermined path with said second path so a predetermined point on said source and a predetermined point on said detector define a succession of translated parallel lines, as said source and said detector move, respectively, through said predetermined path and said second path.

20. Apparatus as claimed in claim 11 wherein said detector is annular in form and has an annular extent of three hundred and sixty degrees.

21. Apparatus as claimed in claim 11 wherein said detector has a portion of an annulus and extends for more than one hundred and eighty degrees but less than three hundred and sixty degrees.

22. Apparatus as claimed in claim 1 wherein said detector is annular in form and extends three hundred and sixty degrees.

23. Apparatus as claimed in claim 1 wherein said detector has an angular extent greater than one hundred and eighty degrees but less than three hundred and sixty degrees.

24. Apparatus for examining an object which comprises a source, a mounting for said source, a detector, a mounting for said detector, said mounting for said source permitting said source to move relative to said object in a predetermined path, said mounting for said detector permitting said detector to move relative to said source and relative to said object in a second path, and means to interrelate said predetermined path with said second path so a predetermined point on said source and a predetermined point on said detector define a succession of translated parallel lines, as said source and said detector move, respectively, through said predetermined path and said second path, throughout a complete examination of a cross section of the object.

* * * * *